(12) United States Patent
Bavaro

(10) Patent No.: US 9,994,688 B2
(45) Date of Patent: *Jun. 12, 2018

(54) IRRADIATION AND POST-CURE PROCESSING OF ELASTOMERS

(71) Applicant: CareFusion 303, Inc., San Diego, CA (US)

(72) Inventor: Vincent Bavaro, Temecula, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/204,958

(22) Filed: Jul. 7, 2016

(65) Prior Publication Data

US 2016/0340486 A1 Nov. 24, 2016

Related U.S. Application Data

(63) Continuation of application No. 14/688,972, filed on Apr. 16, 2015, now Pat. No. 9,394,410.

(51) Int. Cl.
| | |
|---|---|
| *C08F 2/50* | (2006.01) |
| *C08G 64/02* | (2006.01) |
| *C08J 7/12* | (2006.01) |
| *C08G 77/32* | (2006.01) |
| *A61L 29/06* | (2006.01) |
| *B29C 71/02* | (2006.01) |
| *B29C 71/04* | (2006.01) |
| *A61M 39/08* | (2006.01) |
| *B29C 35/08* | (2006.01) |

(52) U.S. Cl.
CPC .............. *C08J 7/123* (2013.01); *A61L 29/06* (2013.01); *B29C 71/02* (2013.01); *B29C 71/04* (2013.01); *C08G 77/32* (2013.01); *C08J 7/08* (2013.01); *A61M 39/08* (2013.01); *B29C 2035/085* (2013.01); *B29C 2035/0877* (2013.01); *C08J 2383/04* (2013.01)

(58) Field of Classification Search
CPC .......... C08J 7/123; C08J 2383/04; C08J 7/08; B29C 71/02; B29C 71/04; B29C 2035/0877; B29C 2035/085; C08G 77/32; C08L 83/04; A61L 29/06; A61M 39/08
USPC .......................................... 522/162, 1; 520/1
See application file for complete search history.

(56) References Cited

U.S. PATENT DOCUMENTS

| | | | |
|---|---|---|---|
| 8,378,004 B2 * | 2/2013 | Angermaier | C08L 83/04 522/134 |
| 8,790,305 B2 | 7/2014 | Haylor et al. | |
| 9,394,410 B1 * | 7/2016 | Bavaro | C08G 77/32 |
| 2008/0166509 A1 * | 7/2008 | Simon | C08L 83/04 428/35.7 |
| 2014/0050871 A1 | 2/2014 | Zhu et al. | |
| 2015/0093530 A1 * | 4/2015 | Ward | A61L 29/06 428/36.9 |

OTHER PUBLICATIONS

Nichols et al, E-Beam vs. Gamma Sterilization, May 23, 2013, http://palmweb.uspto.gov/PalmExternalApps/JavaProxy/jsp/BibDataSheetTolrf.jsp?applicationNumber=15204958, 1-6.*
International Search Report and Written Opinion for Application No. PCT/US2016/026969, dated Jul. 6, 2016, 10 pages.

* cited by examiner

*Primary Examiner* — Jessica Whiteley
(74) *Attorney, Agent, or Firm* — McDermott Will & Emery LLP

(57) ABSTRACT

Processing methods are described for improving the physical properties of elastomeric materials including elastomeric tubing. The methods include heating tubing in a post-cured step for a specified time and at a specified temperature. The methods also include irradiating the tubing with a desired dose of radiation. Embodiments can include treatment of silicon-based elastomers and/or non-silicon-based elastomers. The improved elastomers can be utilized in pumps.

19 Claims, 8 Drawing Sheets

FIG. 2A
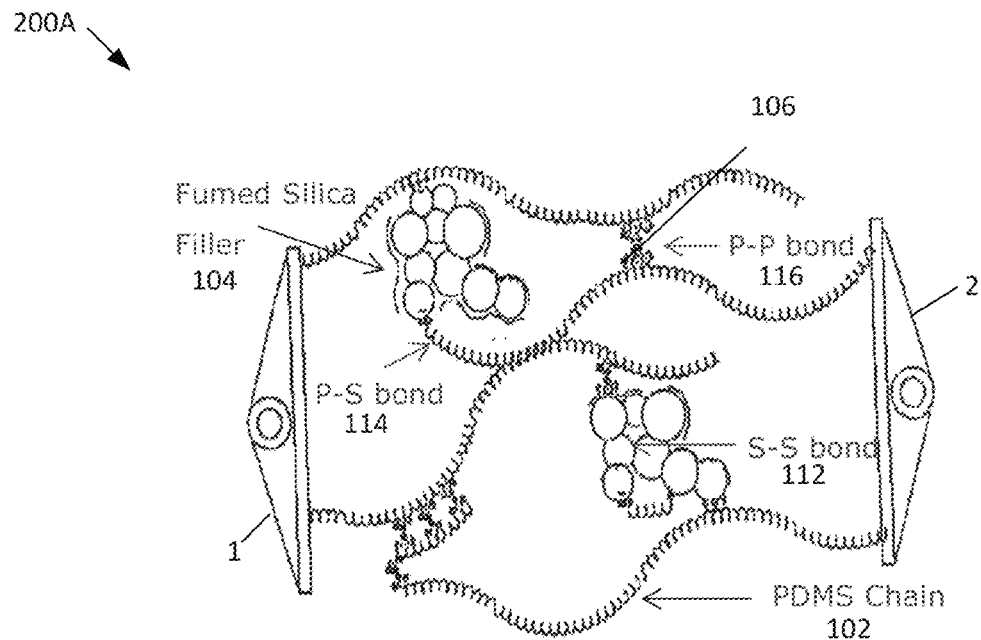
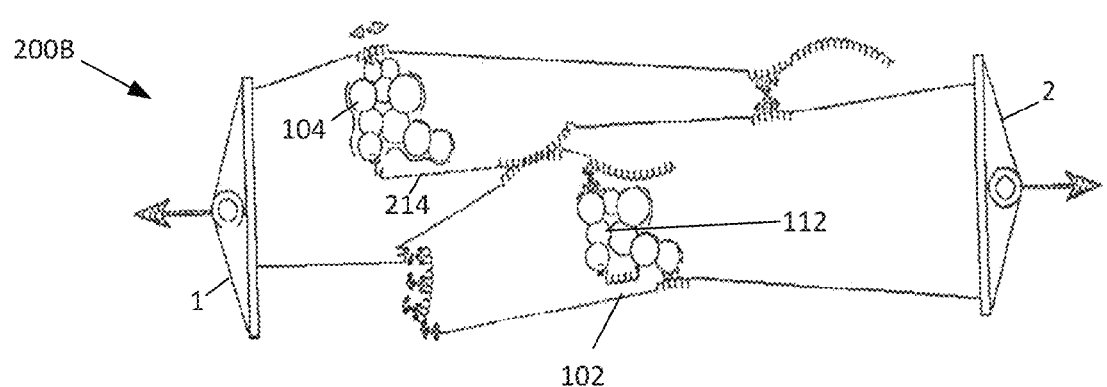
FIG. 2B

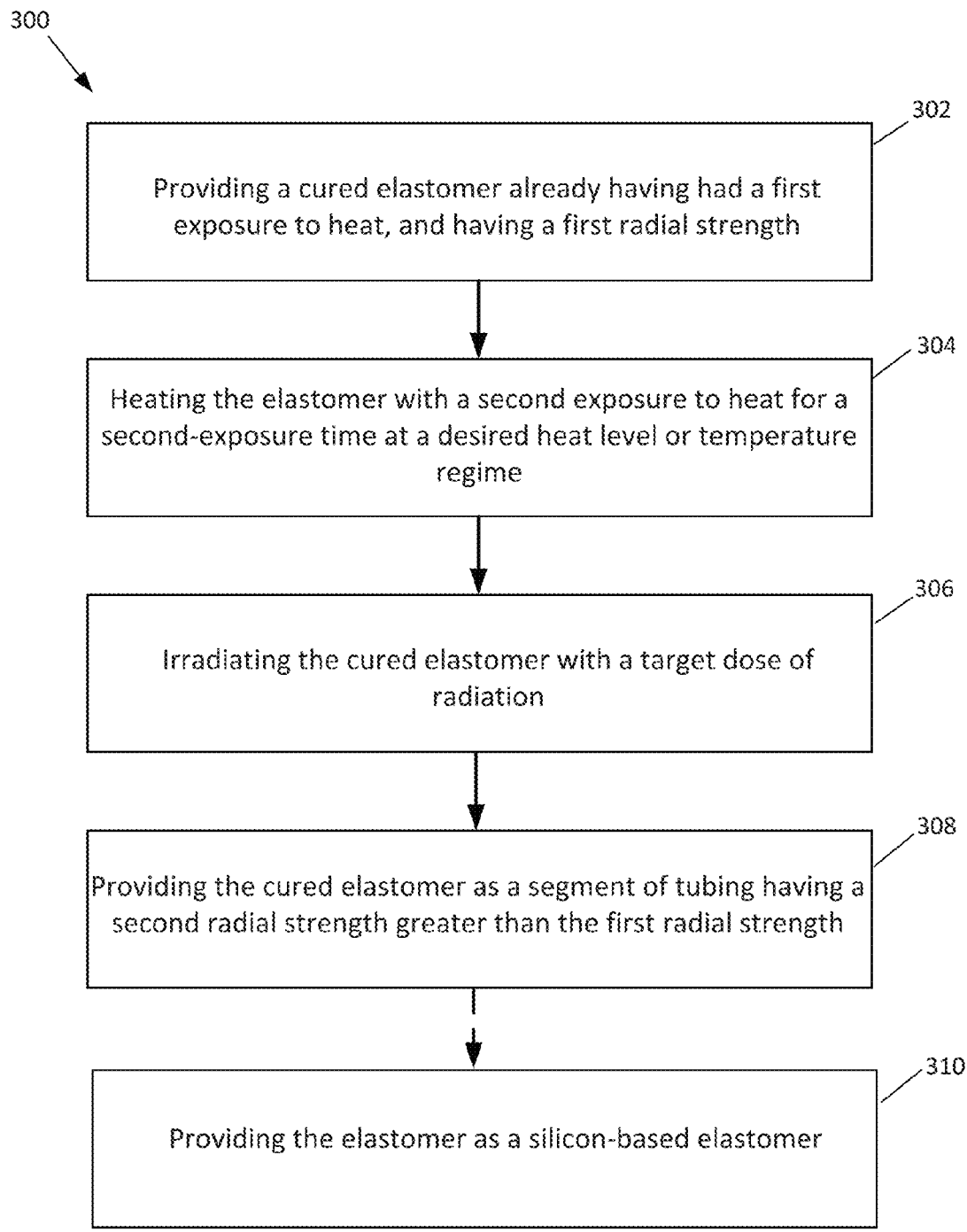

IRRADIATION AND POST-CURE PROCESSING OF ELASTOMERS

CROSS-REFERENCE TO RELATED APPLICATIONS

The present application claims the benefit of priority under 35 U.S.C. § 120 as a continuation of U.S. patent application Ser. No. 14/688,972 entitled "Irradiation and Post-Cure Processing of Elastomers," filed on Apr. 16, 2015, the disclosure of which is hereby incorporated by reference in its entirety for all purposes.

BACKGROUND

Technical Field

This disclosure generally relates to processing of elastomers. More particularly, the present disclosure relates to increasing cross-linking between components of elastomers for producing improvements in mechanical properties.

Description of Related Art

Silicone-based elastomers have been used in the medical industry for various medical device and machine components such as medical tubing. Generally, these materials can present good durability, long life, and are non-reactive with bodily fluids and tissues.

Some prior concerns with the mechanical properties of elastomers used for applications such as medical tubing have included susceptibility to bulging in response to repeated or cyclic variations in fluid pressure within the tubing.

SUMMARY

Processing techniques are described for improving certain mechanical properties of elastomers. Such properties include, e.g., radial or hoop strength, cyclic fatigue strength, etc. These improved mechanical characteristics may be realized with a combination of post-cure heat treatment and irradiation, as described below.

In accordance with an aspect of the present disclosure, post-curing of elastomers can include steps of irradiation and heating, beyond that used for initial curing, for improved physical properties of the elastomers. The second, or "post-cure," exposure to heat can convert or activate additional cross-linking ingredients or constituents, forming or increasing cross-links between constituent components of the elastomer, e.g., the highly reactive surface of silica and adjacent polymers. The second exposure to heat can also facilitate annealing of silica agglomerates. The irradiation process further enhances cross-linking. Exemplary irradiation techniques include gamma ray irradiation and E-beam irradiation.

These, as well as other components, steps, features, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 2A illustrates the structural silicon elastomer model of FIG. 1 in a relaxed state; FIG. 2B illustrates the structural silicon elastomer model of FIG. 1 in a stressed state with positive axial strain shown.

FIG. 3 illustrates a flow chart for an example of a method of processing elastomeric tubing to achieve improved radial strength according to the present disclosure.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
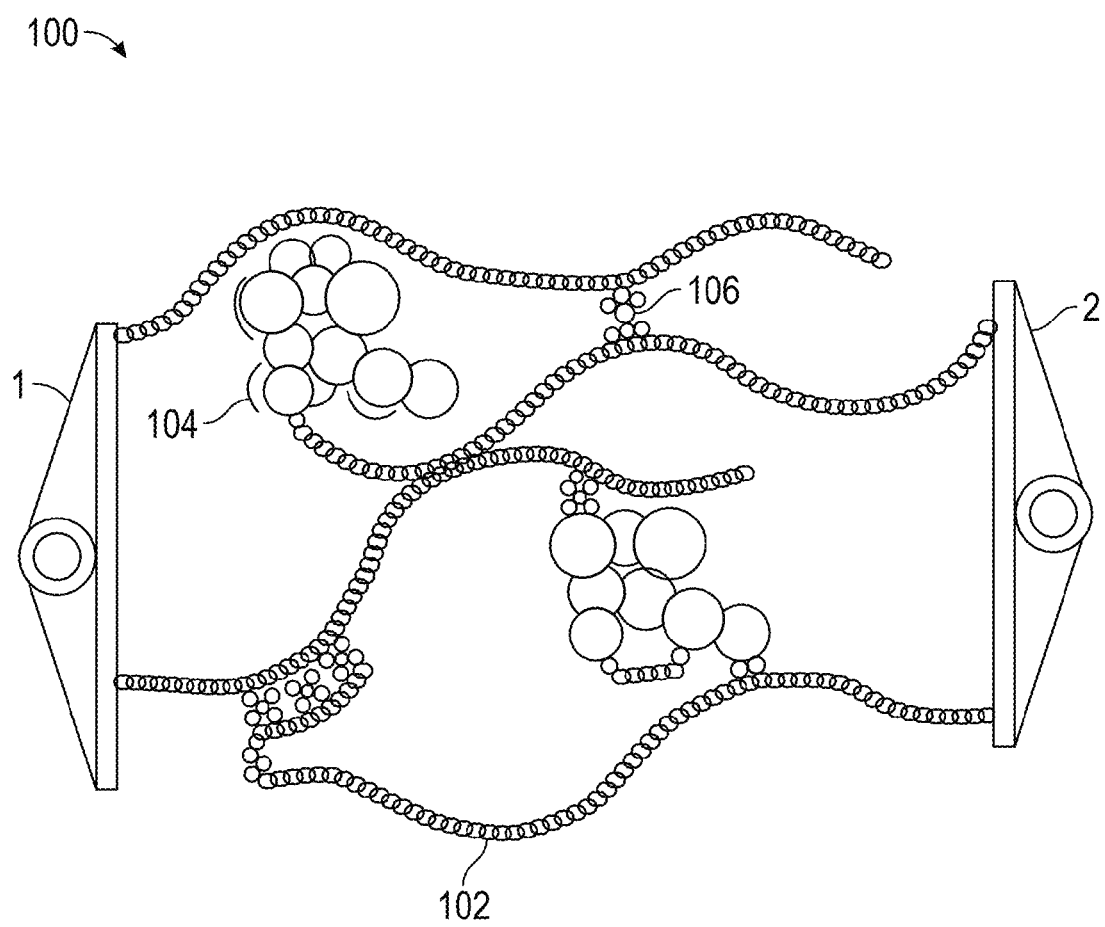
FIG. 1 illustrates a structural silicone elastomer model.

FIG. 1 illustrates a structural silicone elastomer model 100. The elastomer includes polydimethylsiloxane (PDMS), which is highly elastic. The model includes a number of PDMS polymer chains 102. Fumed silica 104 is shown, which acts as a filler and which adds to the rigidity of the elastomer. As shown, the model 100 includes a number of cross-linking agents 106, which act to chemically bond adjacent constituents of the elastomer. A catalyst may also be present, and can serve, with the addition of heat, to initiate chemical bonding. Two holding fixtures 1-2 are also depicted.

FIG. 2A illustrates the structural silicon elastomer model 100 of FIG. 1 in a relaxed or unstrained state; FIG. 2B illustrates the structural silicon elastomer model 100 of FIG. 1 in a stressed state with positive axial strain shown as induced by tension applied to fixtures 1-2. FIGS. 2A and 2B illustrate properties of various bonds within the elastomer: (i) bonds 112, which are extremely brittle; (ii) polymer-to-silica bonds 114, which tend to increase rigidity or durometer; and, (iii) polymer-to-polymer bonds 116, which are extremely ductile and lead to or enhance entanglement and cross-linking.

In accordance with an aspect of the present disclosure, post-curing treatment of elastomers or elastomeric material can include steps of irradiation and additional heating, beyond the heating realized during initial curing, for obtaining improved physical properties of the elastomers. Exemplary embodiments include irradiation and heat treatment of silicon-based elastomers to realize improved burst strength.

In general, the second exposure to heat can convert or activate additional cross-linking ingredients (or constituents), forming cross-links between, e.g., the highly reactive surface of silica and adjacent polymers, e.g., as shown in FIGS. 1-2B. The second exposure to heat can also facilitate annealing of silica agglomerates. The irradiation process further enhances cross-linking.

Exemplary irradiation techniques include use of gamma ray irradiation and E-beam irradiation. Gamma ray irradiation can be obtained by use of Cobalt-60 as a radiation source, and typically operates in excess of 100 MeV. In contrast, E-beam irradiation typically operates in the Key to MeV range. The response to a particular radiation source is polymer and stabilization package dependent. Polymers prone to oxidative degradation fare better to E-beam irradiation due to higher dose rates and shorter exposure times. For example, it might take 271 minutes to attain a desired dosage of 25 kilogray (kGy) for gamma rays compared to under five (5) minutes for E-beam irradiation to accumulate, where kilogray (kGy) is a derived metric (SI) measurement unit of absorbed radiation dose of ionizing radiation, e.g., X-rays. The kilogray is equal to one thousand gray (1000 Gy), and the gray is defined as the absorption of one joule of ionizing radiation by one kilogram (1 J/kg) of matter, e.g., elastomer.

FIG. 3 illustrates a flow chart for an example of a method 300 of processing elastomeric material, e.g., elastomeric tubing, according to the present disclosure. Method 300 includes a step of providing a cured elastomer already having had a first exposure to heat (e.g., during an initial curing process), and having a first radial strength, as shown at 302. The radial strength can alternately be described as "hoop" strength or "burst" strength, the latter referring to a cylinder's resistance to bursting under applied pressure. Method 300 includes a step of heating the elastomer with a second exposure to heat for a second-exposure time at a desired heat level or temperature regime, as described at 304.

Continuing with the description of method 300, a step of irradiating the cured elastomer with a target dose of radiation is included, as shown at 306. While step 306 is shown as occurring after step 304, the step order may of course be reversed. Alternatively, the steps of heating and irradiation may occur simultaneously in whole or in part; further, the heating and irradiation steps may be broken up into substeps, which may occur in any order or simultaneously. Method 300 further includes a step of providing the cured elastomer as a segment of tubing having a second radial strength greater than the first radial strength, as shown at 308. Exemplary embodiments can include using or providing a silicon-based elastomer, e.g., polydimethylsiloxane (PDMS), as the segment of tubing. Method 300 can be used to make elastomeric materials, e.g., pump tubing segments, which can function with improved physical characteristics or properties, such as radial strength, in certain applications such as in medical devices. Of course, other embodiments can include different elastomers, including non-silicon-based elastomers.

FIGS. 4-11 illustrate performance testing and comparisons showing improved physical characteristics or properties of elastomeric tubing prepared in accordance with the present disclosure.

Figure 4:
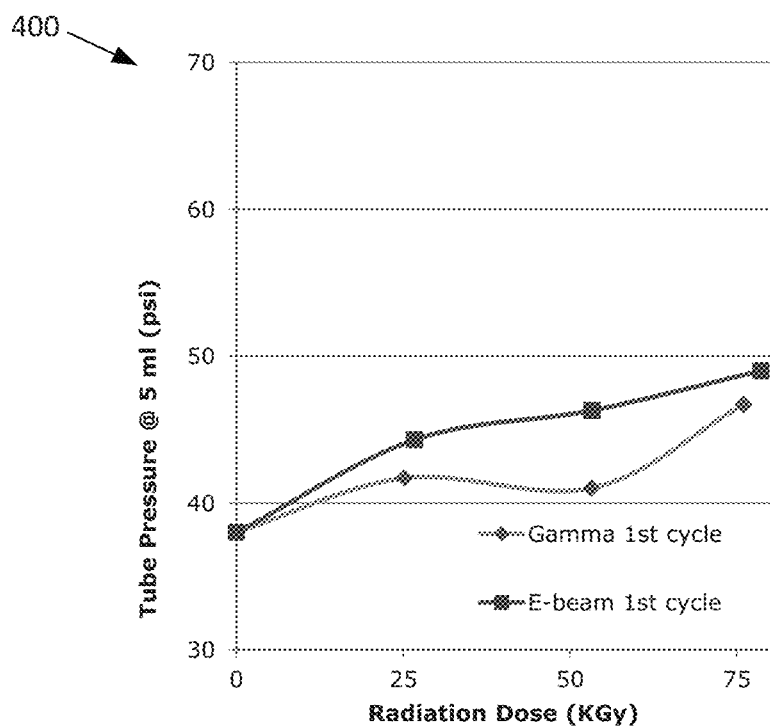
FIG. 4 illustrates a graph of pressure vs. radiation dose for a segment of as-received elastomeric tubing receiving a 5 ml injection volume of liquid.

FIG. 4 illustrates a graph 400 of pressure vs. radiation dose for a segment of as-received elastomeric tubing receiving a 5 ml injection volume of liquid. The material tested was Biosil6 platinum-cured elastomer, a Saint-Gobain trade name for polydimethylsiloxane (PDMS), formed as tubing with inner diameter of 0.130" and wall thickness of 0.03" and having a length of 5.75". Plots are shown for irradiation with Gamma rays (line with diamonds) and for E-beam irradiation (line with squares). As indicated tube pressure, indicative of wall radial strength, increased with increasing radiation dosages.

Figure 5:
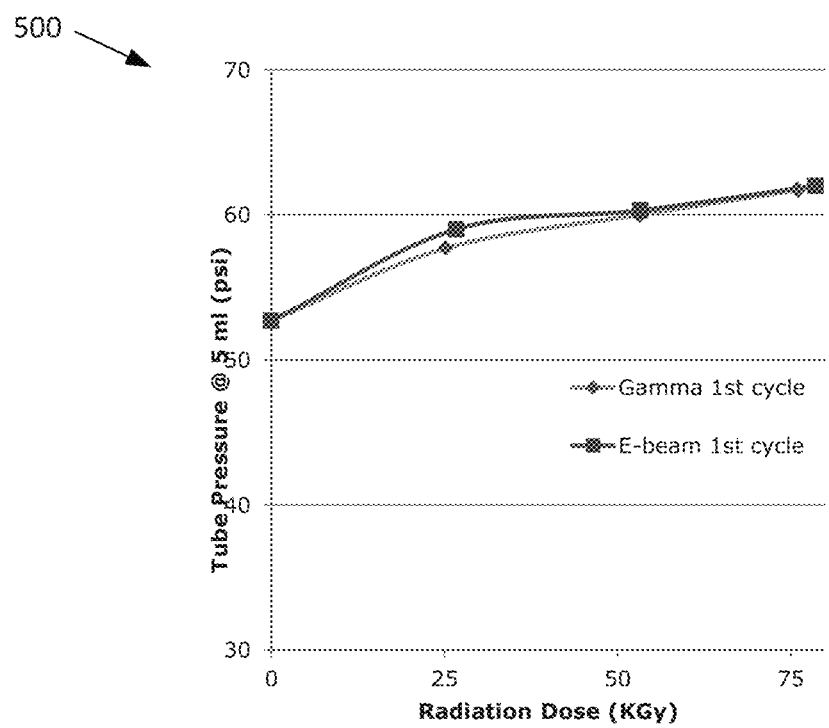
FIG. 5 illustrates a graph of pressure vs. radiation dose for a segment of post-cured elastomeric tubing receiving a 5 ml injection volume of liquid.

FIG. 5 illustrates a graph 500 of pressure vs. radiation dose for a segment of post-cured elastomeric tubing receiving a 5 ml injection volume of liquid after having been subject to a heating treatment, a second heating treatment beyond that occurring for the initial curing process. The material tested was Saint-Gobain Biosil6 platinum-cured elastomer formed as tubing with inner diameter of 0.130" and wall thickness of 0.03" and having a length of 5.75". Plots are shown for irradiation with Gamma rays (line with diamonds) and for E-beam irradiation (line with squares). The post-curing heat treatment consisted of subjecting the tubing to heat at 400° F. for 2 hours in a convention oven. As indicated tube pressure, indicative of wall radial strength, increased with increasing radiation dosages. The indicated values are significantly greater that the values shown in FIG. 4, where tubing with the same material was subjected to just radiation treatment and not the second heat treatment.

Figure 6:
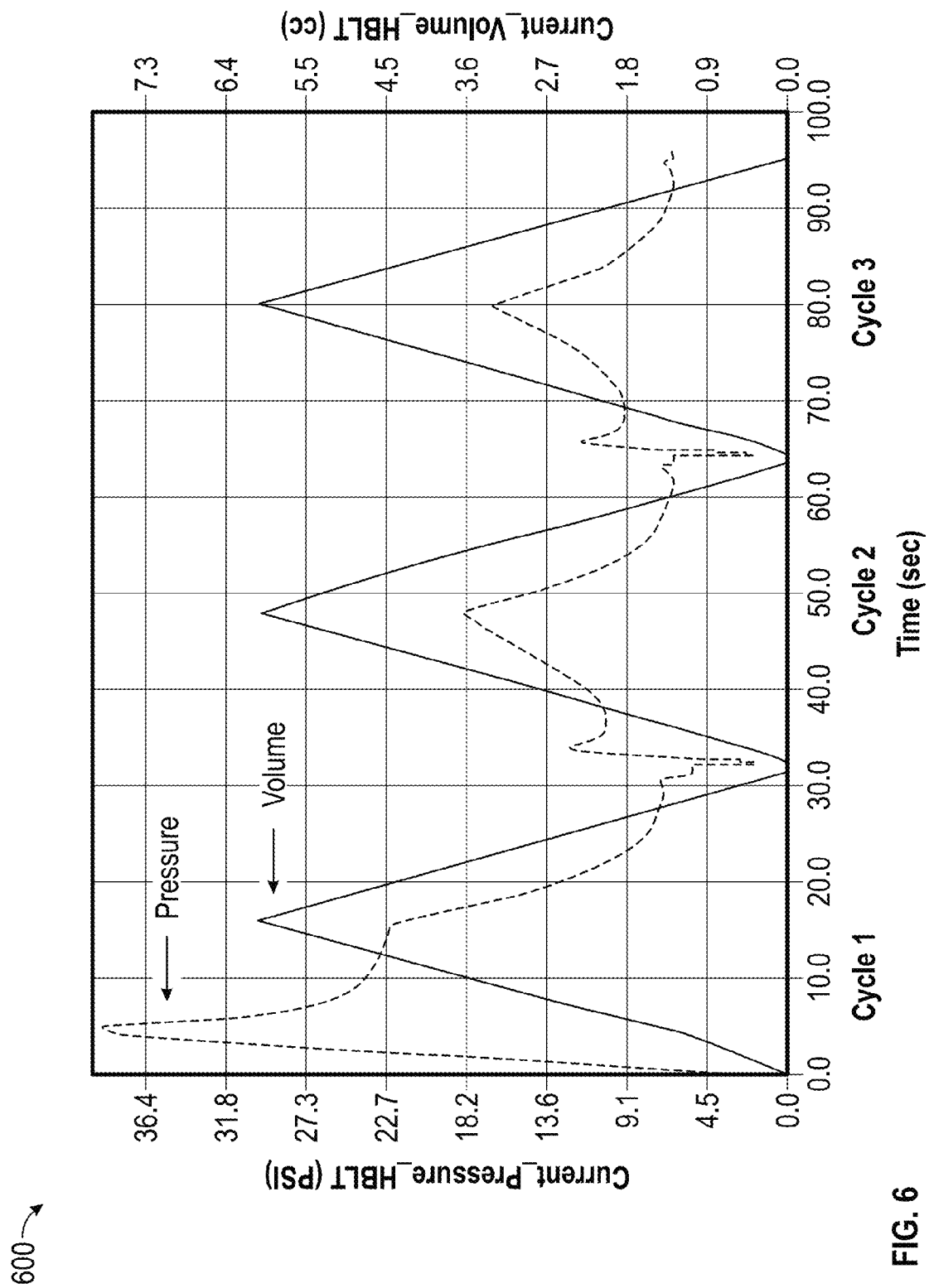
FIG. 6 illustrates a graph of cyclic fatigue data obtained during hydraulic burst-leak testing of examples of strengthened elastomeric tubing processed according to the present disclosure.

FIG. 6 illustrates a graph 600 of cyclic fatigue data obtained during hydraulic burst-leak testing of examples of strengthened elastomeric tubing processed according to the present disclosure. The elastomeric material was Saint-Gobain Biosil6 platinum-cured elastomer, which was subject to a post-cure heat treatment with a duration of two hours at 400° F.; the material was irradiated with a Cobalt 60 Gamma ray source such that the tubing was supplied with a 75 kGy dose of radiation. Peak pressure for three cycles of 5 ml injection volumes is indicated.

Figure 7:
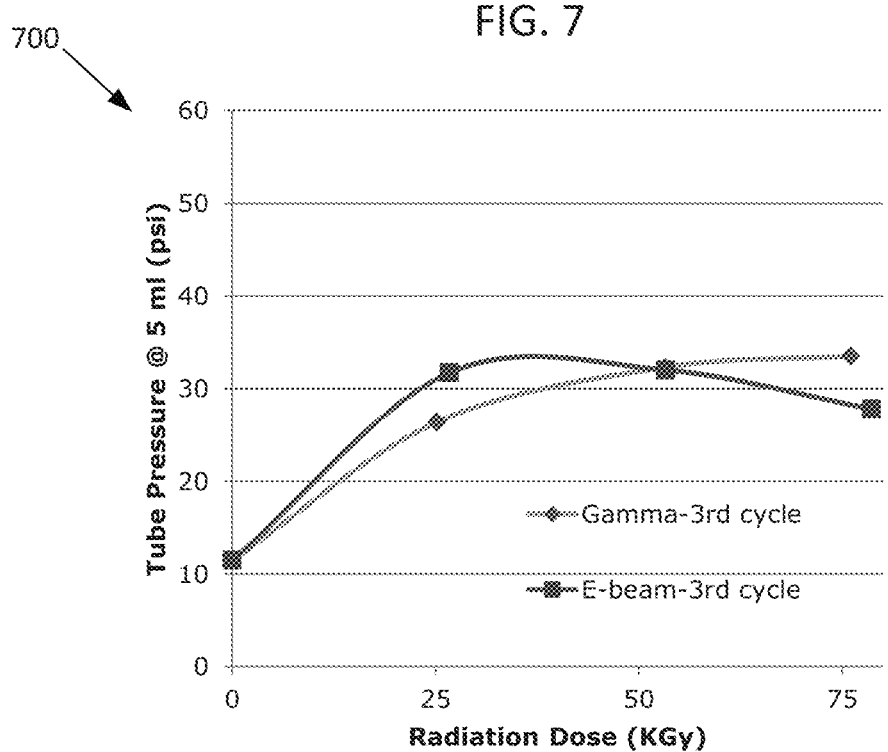
FIG. 7 illustrates a graph of pressure vs. radiation dose for a segment of as-received elastomeric tubing receiving a third-cycle 5 ml injection volume of liquid.

FIG. 7 illustrates a graph of pressure vs. radiation dose for a segment of as-received elastomeric tubing receiving a third-cycle 5 ml injection volume of liquid. The material tested was Biosil6 platinum-cured elastomer, a Saint-Gobain trade name for polydimethylsiloxane (PDMS), formed as tubing with inner diameter of 0.130" and wall thickness of 0.03" and having a length of 5.75". Plots are shown for irradiation with Gamma rays (line with diamonds) and for E-beam irradiation (line with squares). As indicated tube pressure, indicative of wall radial strength, increased with increasing radiation dosages.

It may be noted that in FIG. 7 the tube pressure values for each type of radiation source appear to plateau or actually decline with an increase of radiation does to 75 kGy. This trend implies that no additional cross-linking can occur in the elastomer material, leading to the conclusion that additional heat treatment would not improve the physical properties of the material, including wall radial strength.

Figure 8:
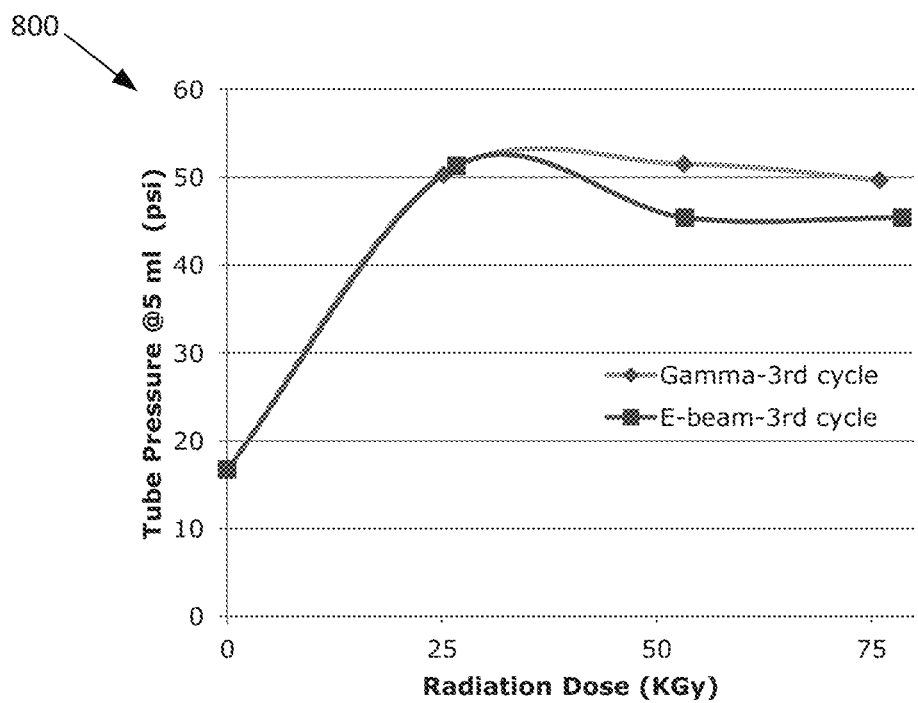
FIG. 8 illustrates a graph of pressure vs. radiation dose for a segment of post-cured elastomeric tubing receiving a third-cycle 5 ml injection volume of liquid.

FIG. 8 illustrates a graph of pressure vs. radiation dose for a segment of post-cured elastomeric tubing receiving a third-cycle 5 ml injection volume of liquid. The material tested was Saint-Gobain Biosil6 platinum-cured elastomer formed as tubing with inner diameter of 0.130" and wall thickness of 0.03" and having a length of 5.75". Plots are shown for irradiation with Gamma rays (line with diamonds) and for E-beam irradiation (line with squares). The post-curing heat treatment consisted of subjecting the tubing to heat at 400° F. for 2 hours in a convention oven. As indicated tube pressure, indicative of wall radial strength, increased with increasing radiation dosages. The indicated values are significantly greater that the values shown in FIG. 7 (despite what FIG. 7 otherwise implies), where tubing with the same material was subjected to just radiation treatment and not the second heat treatment.

Figure 9:
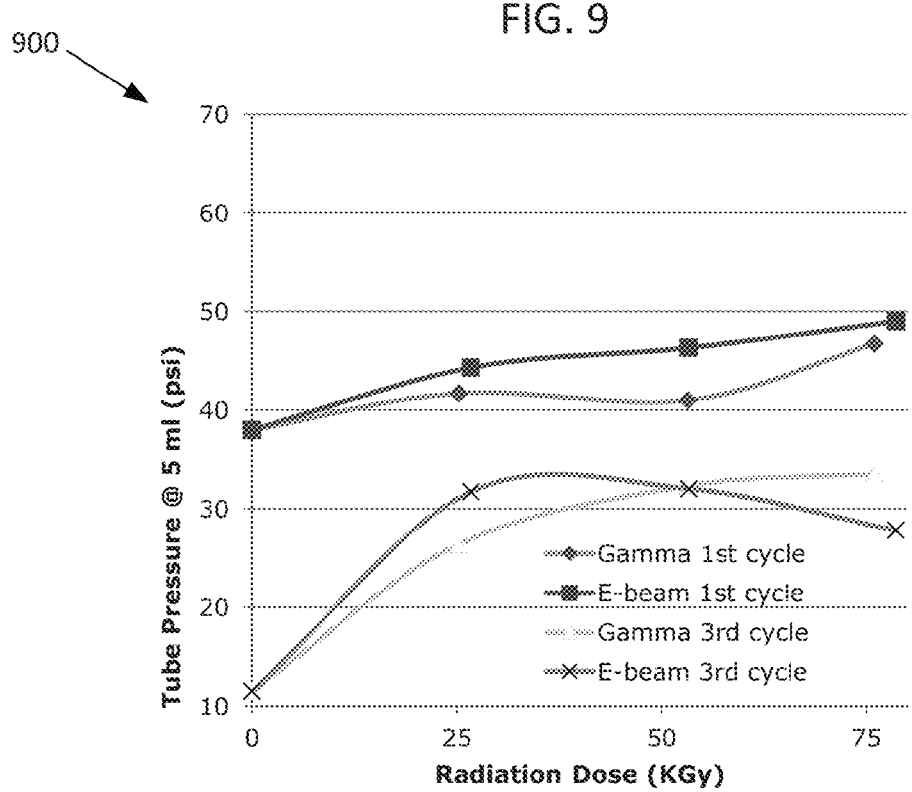
FIG. 9 illustrates a composite graph with the data of FIG. 4 and FIG. 7.

FIG. 9 illustrates a composite graph with the data of FIG. 4 and FIG. 7.

Figure 10:
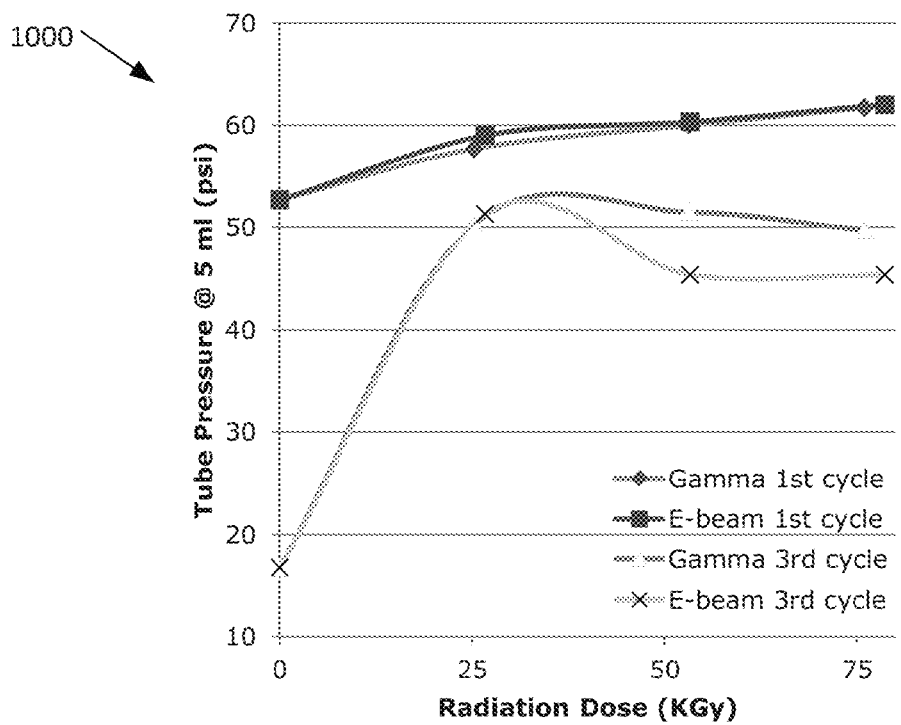
FIG. 10 illustrates a composite graph with the data of FIG. 5 and FIG. 8.
Figure 11A:
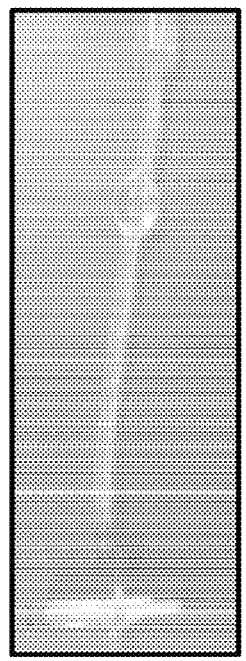
FIG. 11 is a set of photographs showing failure modes of tube segment samples having received 5 ml volumes as, respectively, received (a), irradiated only (b), post-cured only (c), and irradiated and post-cured (d).
Figure 11B:
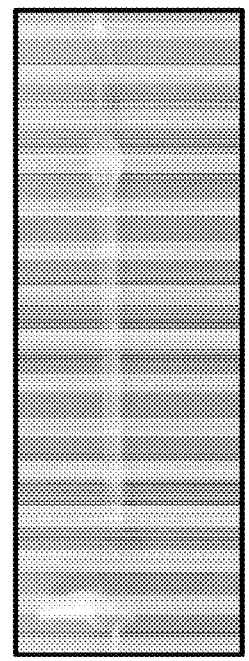
Figure 11C:
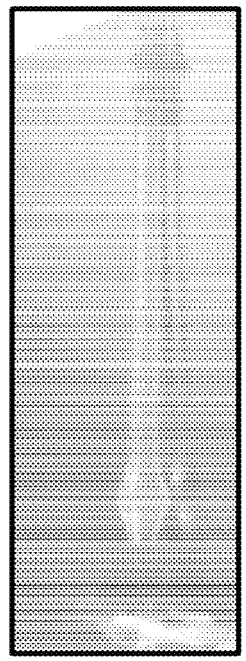
Figure 11D:
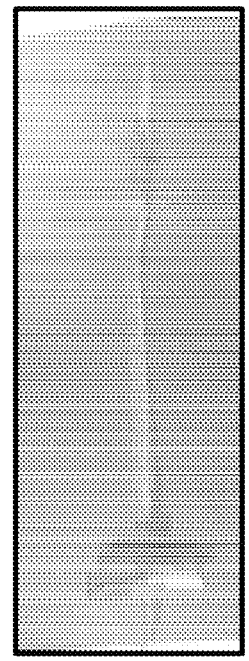

FIG. 10 illustrates a composite graph with the data of FIG. 5 and FIG. 8.

FIG. 11 is a set of photographs showing failure modes of tube segment samples having received 5 ml volumes that are, respectively, as-received (a), irradiated only (b), post-cured only (c), and irradiated and post-cured (d). As can be seen, the irradiate and post-cured tube segment in (d) shows the best performance.

Accordingly, embodiments of the present disclosure can provide for benefits and advantages over prior techniques for making or providing suitable elastomeric materials, e.g., for use in medical applications. Exemplary embodiments can utilize such improved elastomers in the form of tubing segments used in pumps, e.g., as shown and described in U.S. Pat. No. 8,790,305, the entire content of which is incorporated herein by reference.

Unless otherwise indicated, the methods and steps of applying heat, irradiation, and testing that have been discussed herein can be implemented with assistance of computer system configured to perform the functions that have been described herein. Each computer system includes one or more processors, tangible memories (e.g., random access memories (RAMs), read-only memories (ROMs), and/or programmable read only memories (PROMS), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

Each computer system may be a desktop computer or a portable computer, such as a laptop computer, a notebook computer, a tablet computer, a PDA, a smartphone, or part of a larger system, such a vehicle, appliance, and/or telephone system. Each computer system for the control of irradiation and/or heating may include one or more computers at the same or different locations. When at different locations, the computers may be configured to communicate with one another through a wired and/or wireless network communication system.

Each computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

The components, steps, features, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A method, comprising:
providing elastomeric tubing already having had a first exposure to heat, and having a radial strength equal to a first radial strength;
heating the elastomeric tubing with a second exposure to heat; and
increasing the radial strength by irradiating the elastomeric tubing with a dose of seventy-five kilogray to a second radial strength that is greater than the first radial strength.

2. The method of claim 1, wherein the heating comprises heating the elastomeric tubing for approximately two hours at a temperature of approximately four hundred degrees Fahrenheit.

3. The method of claim 1, wherein the heating comprises heating the elastomeric tubing for approximately two hours at a temperature of approximately four hundred degrees Fahrenheit.

4. The method of claim 1, wherein the elastomeric tubing comprises a silicon-based elastomer or a polydimethyl siloxane (PDMS).

5. The method of claim 1, further comprising coupling the irradiated elastomeric tubing having the second radial strength to a pump.

6. The method of claim 1, wherein the irradiating comprises applying gamma-ray irradiation to the elastomeric tubing.

7. The method of claim 1, wherein the irradiating comprises applying E-beam irradiation to the elastomeric tubing.

8. A method of strengthening elastomeric tubing, the method comprising:
providing a segment of the elastomeric tubing already having had a first exposure to heat, and having a first radial strength;
increasing the first radial strength by irradiating the segment with seventy-five kilogray of gamma-ray irradiation; and
providing the irradiated segment as a strengthened segment of elastomeric tubing having a second radial strength greater than the first radial strength.

9. The method of claim 8, wherein the irradiating comprises irradiating the segment with less than fifty kilogray of the gamma-ray irradiation.

10. The method of claim 8, further comprising, prior to the irradiation, heating the segment with a second exposure to heat.

11. The method of claim 10, wherein the heating comprises heating the segment for at least two hours at a temperature of approximately four hundred degrees Fahrenheit.

12. The method of claim 8, further comprising, following the irradiation, heating the segment with a second exposure to heat.

13. The method of claim 12, wherein the heating comprises heating the segment for at least two hours at a temperature of approximately four hundred degrees Fahrenheit.

14. A method, comprising:
providing elastomeric tubing already having had a first exposure to heat, and having a first radial strength;
increasing the first radial strength by irradiating the elastomeric tubing with seventy-five kilogray of E-beam irradiation; and
providing the irradiated elastomeric tubing as a strengthened elastomeric tubing having a second radial strength greater than the first radial strength.

15. The method of claim 14, wherein the irradiating comprises irradiating the elastomeric tubing with less than fifty kilogray of the E-beam irradiation.

16. The method of claim 14, further comprising heating the elastomeric tubing with at least a second exposure to heat.

17. The method of claim 16, wherein the heating comprises heating the elastomeric tubing for at least two hours at a temperature of approximately four hundred degrees Fahrenheit.

18. The method of claim 16, wherein the irradiating and the heating comprise intermittently heating and irradiating the elastomeric tubing.

19. The method of claim 16, wherein the heating comprises heating the elastomeric tubing during the irradiating.

* * * * *